United States Patent [19]

Blacklock et al.

[11] Patent Number: 5,011,942

[45] Date of Patent: Apr. 30, 1991

[54] PROCESS FOR RACEMIZING AN ENANTIOMER OF 5,6-DIHYDRO-4-ALKYLAMINO-4H-THIENO(OR FURO) [2,3-B]-THIOPYRAN-2-SULFONAMIDE-7,7-DIOXIDE

[75] Inventors: Thomas J. Blacklock, Clark; Edward J. J. Grabowski, Westfield; Paul Sohar, Warren, all of N.J.

[73] Assignee: Merck & Co., Inc., Rahway, N.J.

[21] Appl. No.: 474,868

[22] Filed: Feb. 5, 1990

[51] Int. Cl.$^5$ .......................................... C07D 495/06
[52] U.S. Cl. ................................................... 549/23
[58] Field of Search .......................... 564/302; 549/23

[56] References Cited

U.S. PATENT DOCUMENTS

| | | | |
|---|---|---|---|
| 4,096,186 | 6/1978 | Ichikawa et al. | 564/302 |
| 4,226,803 | 10/1980 | Klingler et al. | 549/437 X |
| 4,252,744 | 2/1981 | Bison et al. | 564/302 |
| 4,339,603 | 7/1982 | Raghu et al. | 564/302 |
| 4,677,115 | 6/1987 | Baldwin et al. | 514/432 |

*Primary Examiner*—Frederick E. Waddell
*Assistant Examiner*—Catherine S. Kilby Scalzo
*Attorney, Agent, or Firm*—William H. Nicholson; Joseph F. DiPrima

[57] ABSTRACT

Compounds classified as 5,6-dihydro-4-alkylamino-4H-thieno (or furo) [2,3-b]thiopyran-2-sulfonamide-7,7-dioxide are carbonic anhydrase inhibitors useful in the treatment of ocular hypertension, and most of the carbonic anhydrase inhibitory activity resides in only one of the enantiomers. The undesired enantiomer is utilized by racemization by thermolysis of an N-acyl derivative in a basic environment followed by removal of the acyl group. The racemate may then be resolved into the enantiomers.

18 Claims, No Drawings

PROCESS FOR RACEMIZING AN ENANTIOMER OF 5,6-DIHYDRO-4-ALKYLAMINO-4H-THIENO(OR FURO) [2,3-B]-THIOPYRAN-2-SULFONAMIDE-7,7-DIOXIDE

SUMMARY OF THE INVENTION

This invention is concerned with a process for racemizing the undesired enantiomer of a compound of structural formula I:

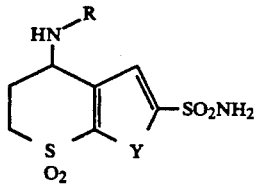

wherein Y is oxygen or sulfur to the racemate from which the desired enantiomer can be obtained by resolution, thereby increasing the yield of the desired enantiomer. Compound I racemate and the enantiomers are carbonic anhydrase inhibitors useful in the treatment of ocular hypertension and glaucoma related thereto. One of the enantiomers is somewhat more active than the racemate or the other enantiomer.

The process comprises acylation of the amino function of the undesired enantiomer, thermolysis in a basic environment to form the racemate and removal of the acyl group.

BACKGROUND OF THE INVENTION

Compounds of structural formula I

I are known to be carbonic anhydrase inhibitors useful in the treatment of ocular hypertension and glaucoma by topical ocular administration, as disclosed by Baldwin et al. in U.S. Pat. No. 4,677,115 (1987) the disclosure of which is incorporated herein by reference.

It has been found that the dextro-or S(+)-enantiomer of I wherein R is isobutyl and Y is sulfur manifests most of the activity found in the racemate. Accordingly, the levo-enantiomer being of no use would be discarded. Now, however, with the present invention, there is provided a means of utilizing the levo-enantiomer by racemizing it followed by resolution of the racemate to produce additional dextro-enantiomer. The resulting levo-enantiomer may, of course, be recycled through additional racemizations/resolutions.

It is an object of this invention to provide a process for racemization of the pharmacologically less active enantiomer of Compound I.

It is a further object of this invention to provide a process to increase the effective synthetic yield of the more useful enantiomer of Compound I.

DETAILED DESCRIPTION OF THE INVENTION

This invention is concerned with a novel process for the racemization of an enantiomer of a compound of structural formula I:

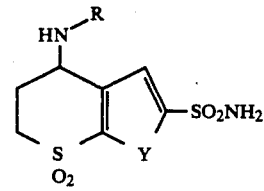

wherein Y is —O— or —S— and R is $C_{1-8}$ alkyl, either straight or branched chain.

The novel process may be depicted as follows:

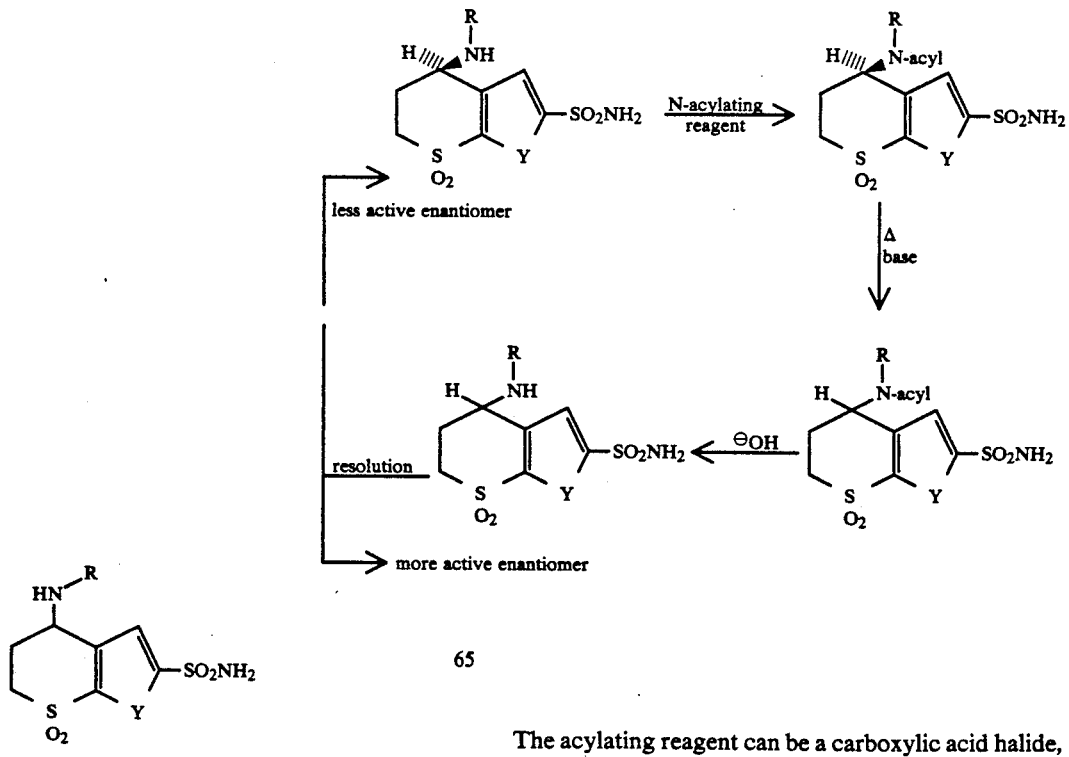

The acylating reagent can be a carboxylic acid halide, such as chloride or bromide, or can be a carboxylic acid anhydride. The reaction conditions can be any standard conditions known in the art for forming N-acyl derivatives such as an acid halide in the presence of an acid acceptor such as an organic amine like triethylamine, pyridine or the like, the organic amine serving as the reaction solvent or merely being present in a second solvent such as ethyl acetate, THF or dichloromethane.

Alternatively the acylation may be achieved by the action of an acid anhydride on the free base in the presence of an aprotic solvent such as ethyl acetate. The reaction proceeds at a temperature of about 10° to 30° C. and is complete in about 5 to 20 hours, conveniently at room temperature overnight.

The racemization is conducted by dissolving the acylamide in dry formamide and heating at about 150° to 180° C. for about 1 to 7 hours.

Alternatively, racemization can be conducted by dissolving the acylamide in a protic solvent such as a $C_{1-3}$alkanol, DMF or the like containing an anhydrous base such as a tri($C_{1-3}$alkyl)amine or an alkali metal $C_{1-3}$alkoxide, and heating at 100°–150° C. for about 1 to 7 hours.

After isolation by diluting largely with water and collecting the precipitate of racemized product, the N-acyl group is removed by suspending the precipitate in methanol, adding sodium hydroxide solution and heating at about 40° to 70° C. for about 0.5 to 3 hours.

If the solvent of racemization is compatible with subsequent hydrolysis conditions, then isolation of the racemized product is not necessary; hydrolysis can be effected by the addition of about 35–60% aqueous sodium hydroxide solution.

The identity of the acyl moiety is not critical, the only requirements being that the acyl group survive the thermolysis and that it be fairly easily removable after the thermolysis. Acyl groups such as trifluoroacetyl, formyl, acetyl, chloroacetyl, di- or tri-chloroacetyl, or mono- or difluoroacetyl are useful, but the trifluoroacetyl is preferred.

EXAMPLE (+/−)-5,6-Dihydro-4-(2-methylpropyl)amino-4H-thieno[2,3-b]thiopyran-2-sulfonamide-7,7-dioxide

Step 1: First Resolution (a) Preparation of (+)-5,6-Dihydro-4-(2-methylpropyl)amino-4H-thiopyran-2-sulfonamde-7,7-dioxide Hemi(+)-di-p-toluoyl-D-tartarate, 2

Reaction

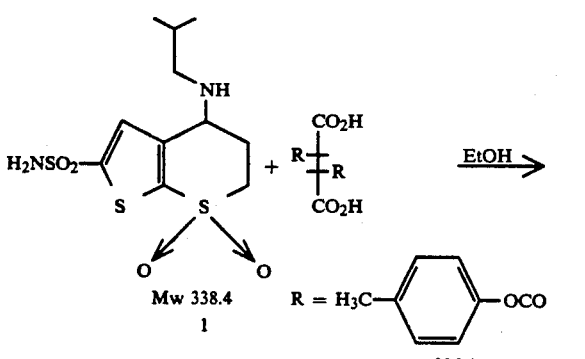

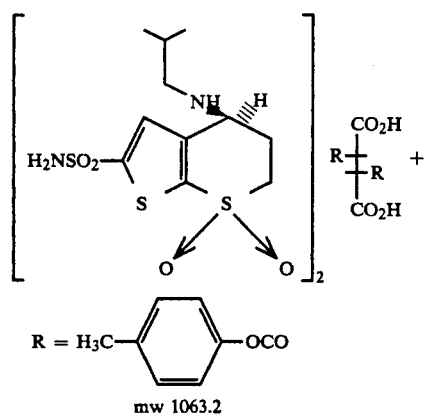

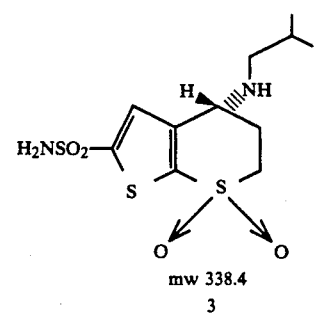

Materials

| 95% ethanol solution of 1 (45 mg/mL, 500 mL) | 22.6 g | 0.067 mol |
| --- | --- | --- |
| (+)-Di-p-toluoyl-D-tartaric acid monohydrate ethanol (95%) | 6.87 g | 0.017 mol |

Experimental

To a 1 liter round bottomed flask equipped with a mechanical stirrer was charged a solution containing 1 (22.6 g, 0.067 mol) in 95% ethanol (45 mg/mL, 500 mL). (+)-Di-p-toluoyl-D-tartaric acid monohydrate (6.87 g, 0.017 mol) was dissolved in warm 95% ethanol (50 mL) and added to the stirred solution of free base 1 with a 75 mL final rinse of 95% ethanol. (A total of 625 mL of 95% ethanol was used giving a final concentration of the free base 1 of 32–37 mg/mL). The homogeneous solution was stirred at ambient temperature for 18 hours. Crystallization ensued within 10 minutes.

The batch was then filtered using filtrate to rinse in the heavy cake. The filter cake was not washed with fresh ethanol and was dried at 40° C. in vacuo to afford 16.81 g of a free flowing white powder D-hemitartrate derivative, assayed at 60% ee. The filtrate was set aside for subsequent "exhaustive" resolution described below.

(b) Recrystallization of 2

Materials

| ethanol, 95% | 400 mL |
| --- | --- |

Experimental

The D-hemitartrate derivative 2 above was recrystallized from a minimum amount of refluxing 95% ethanol (approximately 400 mL), cooled to ambient temperature for 18 hours and filtered. The filter cake was rinsed with 95% ethanol (50 mL) and dried in vacuo at 40° C. to constant weight; yield: 11.7 g (33%) of hemitartrate with >99.5% ee. The combined filtrate and wash was set aside for subsequent use in the exhaustive resolution described below.

(c) Preparation of (+)-5,6-Dihydro-4-(2-methylpropyl)amino-4H-thieno-2-sulfonamde-7,7-dioxide hydrochloride, 4

Reaction

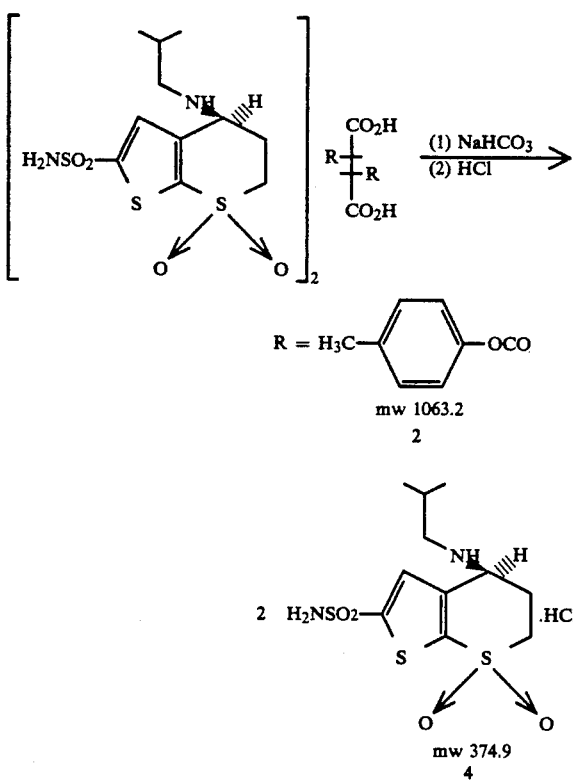

Materials

| | | |
|---|---|---|
| (+)-5,6-Dihydro-4-(2-methyl-propyl)amino-4H-thieno-2-sulfonamide-7,7-dioxide Hemi (+)-Di-p-toluoyl-D-tartrate (94.6 assay %), 2 | 10.63 g | 9.5 mol |
| hydrochloric acid (12N) | 1.6 mL | 19.2 mmol |
| ethyl acetate | 250 mL | |
| sodium sulfate | 25 g | |
| saturted sodium bicarbonate | 153 mL | |
| n-propanol | 340 mL | |
| hexane | 10 mL | |

Experimental

In an extractor was placed ethyl acetate (200 mL), saturated sodium bicarbonate (153 mL) and the delumped hemitartrate, 2, (10.63 g 10 mmol). The mixture was stirred and warmed to 45° C. until two clear layers formed.

The lower aqueous layer was separated, back extracted with ethyl acetate (50 mL), and the organic layers combined. The ethyl acetate product layer was then washed with brine (50 mL), dried over sodium sulfate and filtered. The sodium sulfate filter cake was washed with ethyl acetate (50 mL) and the wash combined with the filtrate. The ethyl acetate solution of 4 free base was concentrated in vacuo (bath temperature 40°-45° C.) to 35 mL. The ethyl acetate concentrate was then flush-concentrated with n-propanol (250 mL) and adjusted to a final volume of 80 mL with n-propanol, such that less than 5 vol % ethyl acetate remained and the concentration of free base was 78-82 mg/mL. The n-propanol solution of free base was then warmed to 50°-55° C.

The warm n-propanol solution of the free base was adjusted to KF 15-17 mg/mL with the addition of approximately 1.6 mL water. Concentrated hydrochloric acid (12N, 1.6 mL, 19.2 mmol) was then added with stirring to the warm solution. The solution was further warmed to 65°-70° C., seeded (100 mg), and stirred for 1 hour at 70° C.

The crystallized mixture was stirred at ambient temperature overnight. The thick slurry was filtered and the product filter cake was washed with n-propanol (10 mL) followed by a displacement wash with hexanes (10 mL). The white solid was dried at 45°-50° C. to afford 6.47 g of 4 in 93% yield (mp 220°-223° C.).

The mother liquors and wash from the crystallization may be recycled into the beginning of this Step after the n-propanol/hexanes has been exchanged for ethyl acetate.

Step 2: Second, "Exhaustive" Resolution:

(a) Crystallization of the R enantiomer

Reaction

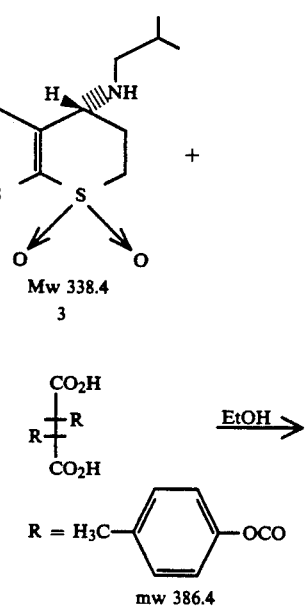

-continued

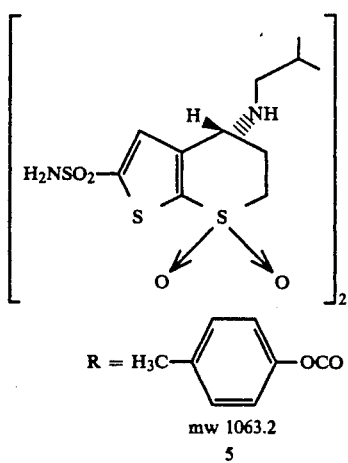

mw 1063.2
5

Materials

| | | |
|---|---|---|
| Mother liquors from Step 1c above; 500 mL @ 22.6 mg/mL free base (R:S ratio 74.6:25.4) | 11.31 g | 33 mmol |
| Di-p-toluoyl-L-tartaric acid monohydrate (97%) | 5.21 g | 12.5 mmol |
| 95% ethanol | 300 mL | |
| 50% satd. NaHCO$_3$ | 50 mL | |
| ethyl acetate | 300 mL | |
| Na$_2$SO$_4$ | | |

Experimental

The hemitartrate crystllation liquors and washes from the 1st resolution and recrystallization (Steps 1b and 1c) were concentrated under vacuum (bath temp 40°–45° C.) to 25–30 mg/mL of isomer mixture as free amine base (KF=4.4%). To this was added di-p-toluoyl-L-tartaric acid monohydrate (5.21 g, 0.0125 m).

The charge of di-p-toluoyl-L-tartaric acid was determined by the ratio of R:S enantiomers and the total amount of free amine base. Charge=((% R X Total Enantiomeric Base Content X 0.5)/338.4) X 404.38. The slurry was heated to 73°–75° C. for 0.5 hours, cooled rapidly to 30°–35° C. and filtered warm (filter jacket at 30°–35° C.). The filter cake was washed with one bed volume of 95% ethanol.

Drying in vacuum at 45°–50° C. to constant weight afforded 9.25 g of R-enantiomer L-hemitartrate @ >99% R ee, (70.5% of available R enantiomer). The cake was set aside for use in the latter racemization sequence.

(b) Neutralization and Crystallization of Crude S-Enantiomer Hemitartrate

Reaction

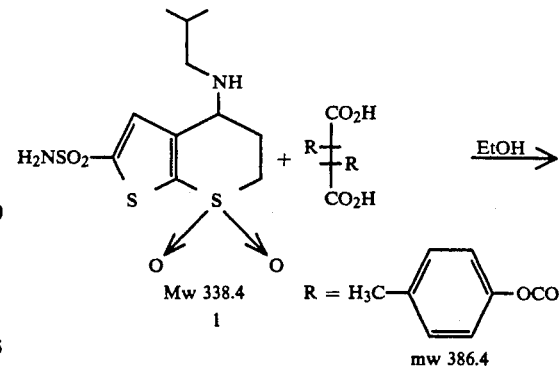

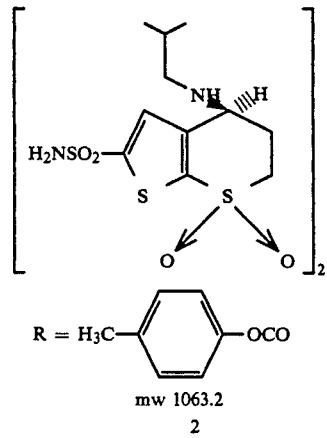

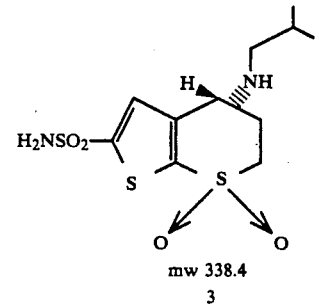

mw 338.4
3

Materials

| | | |
|---|---|---|
| Ethyl acetate solution of essentially racemic free base from Step 2a | (1.44 g S enantiomer, 4.24 mmol S) (2.66 g S + R, 7.86 mmol S + R) | |
| Di-p-toluoyl-D-tartaric acid (97%) | 0.88 g | 2.12 mmol |
| 95% ethanol | 13 mL | |

Experimental

The combined filtrate and wash from the "R" hemitartrate isolation containing an approximate 1:1 ratio of R:S enantiomers was replacement concentrated with ethyl acetate (~250 mL) such that <2 mole % ethanol remained. The volume was then adjusted to 75 mL (32–37 mg/mL) and the mixture washed with 50% satd. NaHCO$_3$ (50 mL) to break the tartrate salt. The aqueous layer was then back extracted with 25 mL of ethyl acetate to recover any remaining base and the organic layers were combined. The ethyl acetate solution of free base was then washed with water (25 mL).

The ethyl acetate solution of free base was replacement concentrated with 95% ethanol (~250 mL) such that <5 mole % ethyl acetate remained and the concentration of (S)-enantiomer was 45 mg/mL (KF=5%) at a total solution volume of 60 mL. To this solution was added di-p-toluoyl-D-tartaric acid (0.88 g, 2.12 mmol) dissolved in 13 mL of warm 95% ethanol. The solution was seeded with 20 mg of (s)-enantiomer D-hemitartrate and stirred at room temperature overnight. The slurry was filtered and the filter cake washed with mother liquors to afford 2.29 g of crude D-hemitartrate (titration 94.4%; 95.2% ee S or a 74.4% recovery of available (S)-enantiomer from the combined liquors). This material was then subjected to a recrystallization as outlined in Step 1b.

The mother liquors from the "S" hemitartrate formation were combined and set aside for use in the racemization sequence (Step 1) below.

Final product mother liquors may be recycled directly into Step 1c after the n-propanol/hexanes has been exchanged for ethyl acetate.

Step 3: Racemization:
(a) Recovery of Free Base
Reaction

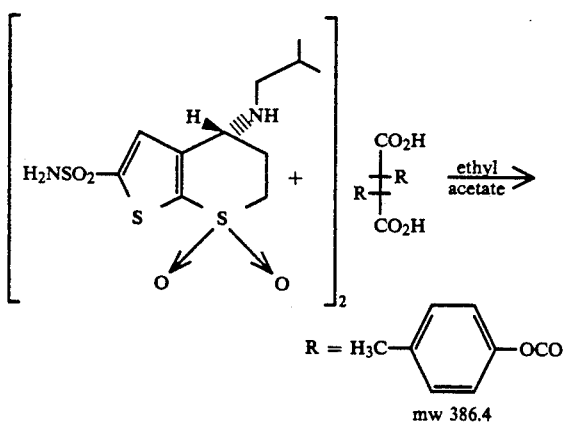

Materials

| resolution rejects from Steps 1a, 2b, and 2a | | 1.3 mol |
|---|---|---|
| ethyl acetate | 20 L | |
| satd. aqueous NaHCO₃ | 2 L | |
| satd. aqueous NaCl | 1 L | |
| MgSO₄ | 150 g | |

Experimental

The crystallization mother liquors (15.8 L) from steps 1a, 1b, 2a and the isolated R-enantiomer L-hemitartrate containing approximately 1.3 moles of 5,6-dihydro-4-(2-methylpropylamino)-4H-thieno [2,3-b]thiopyran-2-sulfonamide-7,7-dioxide as a 2:1 R:S enantiomeric mixture and 0.34 moles of (+)-di-p-toluoyl-D-tartaric acid in ethanol were concentrated in vacuo and the residual ethanol was replaced with ethyl acetate with repeated flushes. Finally, the thick brown slurry was suspended in 3 L of ethyl acetate and 2 L of saturated sodium bicarbonate solution in a 12 L stirred separator. When the two layers had cleared the aqueous portion was drained off and reextracted with 1 L of ethyl acetate, and then the combined organic extracts were washed with 1 L of saturated sodium chloride solution and dried over 150 g of magnesium sulfate. The filtered yellow solution (4 L) was assayed by hplc at 436 g (1.29 moles) of free base. However, its KF was >10 mg/mL indicating high water content, and so the solution was flushed with 2×4 L of ethyl acetate until a KF of 1.4 mg/mL was attained.

(b) Acylation
Reaction

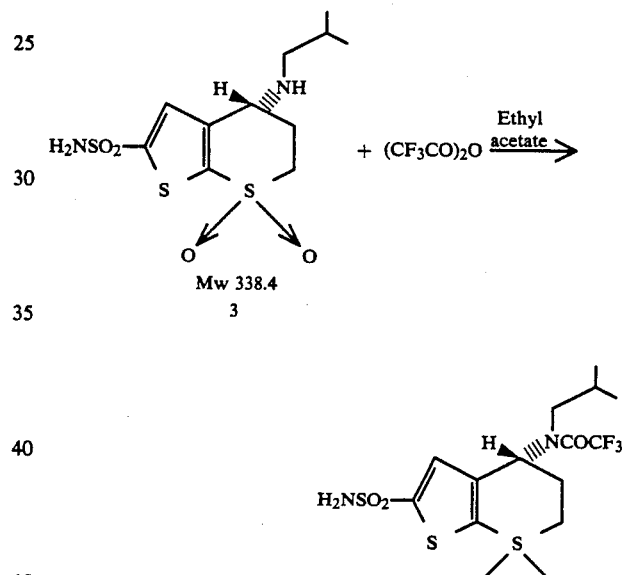

Materials

| free base from Step 3a, 3 | | 1.29 mol |
|---|---|---|
| trifluoroacetic anhydride | 298 g | 1.42 mol |
| ethyl acetate | 8 L | |
| diethyl ether | 4 L | |
| hexanes | 1 L | |

Experimental

The flask containing the free base from Step 3 above was equipped with a dropping funnel, N₂ inlet and a cooling bath for the slow addition of 200 mL (298 g, 1.42 moles) of trifluoroacetic anhydride at 10°-15° C.

This normally fast reaction was stirred overnight at room temperature before it was concentrated and flushed with ethyl acetate/ethanol (4:1) mixture. The thick residue was diluted with 4 L of diethyl ether and the resulting slurry was aged with stirring for 1 hour before filtration. The solids were washed with more ether and hexane and air dried to 600 g (theory 560 g).

(c) Thermolysis Reaction

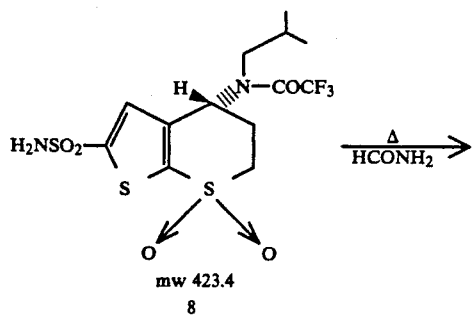

mw 423.4
8

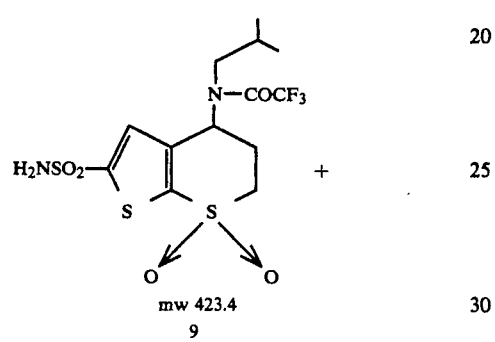

mw 423.4
9

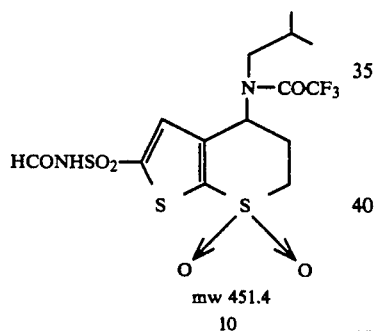

mw 451.4
10

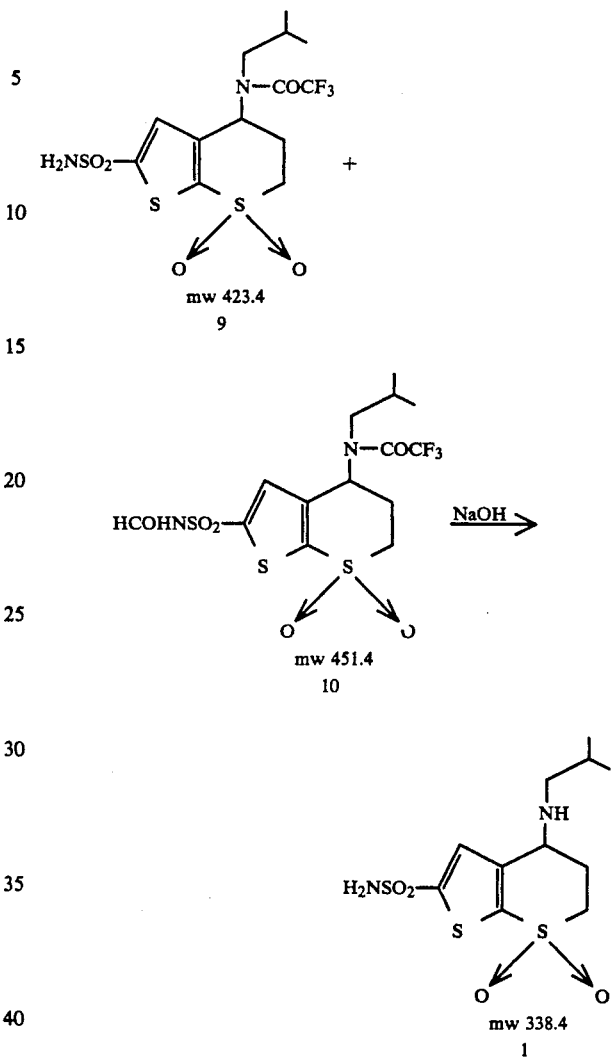

Materials

| | | |
|---|---|---|
| N-acyl product from Step 3b | | 1.29 mol |
| formamide (KF < 0.1 mg/mL) | 1.1 L | |
| water | 6 L | |

Experimental

The entire amount of the crude wet acylation product from Step 3b above was dissolved in 1.1 L of dry formamide in a 5 L round-bottomed flask equipped with a mechanical stirrer, heating mantle, $N_2$ purge and thermometer. As the brown solution was heated it was purged several times. Then the temperature was held at 160°–170° C. for 2.5 hours.

The brown reaction mixture was allowed to cool to 100° C. and then added in a thin stream to 6 L of vigorously stirred water at room temperature. The resulting precipitate was stirred overnight and filtered. The solids were washed with water and air dried.

(d) Hydrolysis Reaction

Materials

| | | |
|---|---|---|
| crude N-acyl racemate from Step 3c above | | 1.29 mol |
| methanol | 1 L | |
| 50% sodium hydroxide | 250 mL | |
| ethyl acetate | 6 L | |
| water | 3 L | |
| conc. hydrochloric acid | 160 mL | |
| Satd. aqueous NaCl | 1 L | |
| Darco KB | 25 g | |
| magnesium sulfate | 200 g | |

Experimental

The wet racemization products from Step 3c were suspended in 1 L of methanol in a 5 L round-bottomed flask equipped with mechanical stirrer, heating mantle, thermometer an $N_2$ inlet. To the stirred mixture was added 250 mL (380 g, 4.75 moles) of 50% sodium hydroxide solution. No cooling was necessary as the exotherm raised the temperature only to 40° C., and then the mixture was heated at 50°–55° C. for 1 hour.

The cooled reaction mixture was poured with stirring into 3 L of ethyl acetate and 3 L of water in a 12 L separator. The pH of the stirred biphasic system was adjusted from 11.5 to 8.1 with concentrated aqueous hydrochloric acid (160 mL). The layers were separated, and the aqueous portion was extracted with 3 L of ethyl acetate. The combined organic extracts were washed with 1 L of saturated NaCl solution and then stirred with 25 g of Darco KB and 200 g of magnesium sulfate. After filtration the 10.6 L solution was found to contain 0.954 moles of product by hplc and 1.044 moles by titration (yield 74–81%).

(e) Isolation Reaction

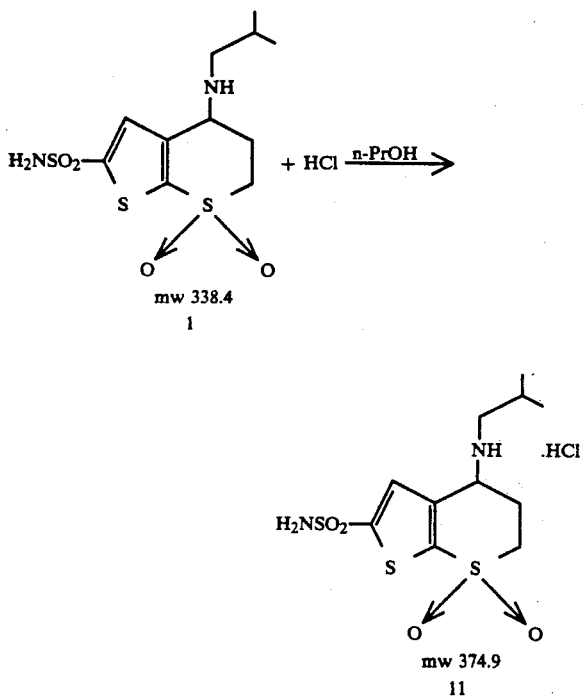

Materials

| ethyl acetate solution of 1 free base | 0.954 mol | |
|---|---|---|
| n-propanol | 9 L | |
| conc. hydrochloric acid (11N) | 95 mL | 1.044 mol |
| hexanes | 1 L | |
| water | 382 mL | |

Experimental

For the isolation of racemate hydrochloride salt the ethyl acetate solution of the racemized free base was concentrated in vacuo. The residue was flushed with 1 L of n-propanol and then dissolved in 5 L of the same solvent. With good stirring 95 mL (1.044 moles) of 11 N hydrochloric acid was added and the resulting crystalline HCl salt was aged with stirring overnight.

In this experiment the crystals were collected and washed free of yellow color with n-propanol and with hexanes. The dried hygroscopic solid (382 g) was redissolved in 382 mL of water and 1 L of n-propanol with heating, then to the cooled solution more n-propanol (820 mL) and seeds were added to induce crystallization. The resulting heavy crystallization mixture was, however, still in the lower melting form. A facile conversion to the higher melting form was achieved by heating up the whole mixture to 90° C. for 10 minutes. After stirring at 20° C. for 2 hours the fine needles were filtered off, washed with n-propanol and hexanes and dried at 85° C. 0.1 min/17 hours. The yield of racemate HCl salt was 340 g (70%); mp 270°–272° C.

In an alternate procedure for the Racemization (3(c)), Hydrolysis (3(d)) and Isolation (3(e)), a 2.0 g portion of the air-dried N-trifluoroacetyl derivative of the R enantiomer was heated in an ethylene glycol (4 ml) solution in the presence of 0.66 ml of triethylamine (4.7 mmoles) at 125°–135° C. for 4 hours. To the cooled solution was added 1.0 ml (19 mmoles) of 50% sodium hydroxide solution and heated again at 50°–55° C. for 5 hours to effect hydrolysis. The cooled solution was diluted with 30 ml of ethyl acetate and 15 ml of water. The pH of the stirred mixture was adjusted to 8 by the addition of 12n hydrochloric acid. The layers were separated and the aqueous portion was washed with 15 ml of ethyl acetate. The combined organic extracts were filtered with 0.5 g of MgSO4 and 50 mg of charcoal. To the stirred filtrate was added 0.4 ml of 12N hydrochloric acid, the mixture was concentrated to half volume, and the solids were collected on a funnel. After washing with ethyl acetate and air drying, 0.47 g (83%) of racemate HCl was obtained; mp 270°–272° C.

(4) Recycle

The racemate prepared as above was introduced to Step 1a for recycle.

Following the procedures substantially as described in the foregoing Example but substituting for the 5,6-dihydro-4-(2-methylpropyl)amino-4H-thieno [2,3-b]thiopyran-2-sulfonamide-7,7-dioxide used therin the corresponding furo[2,3-b]thiopran, or thieno or furo compounds wherein the 2-methylpropyl is replaced by ethyl, n-propyl, isopropyl, n-butyl, t-butyl, n-pentyl, 2-methylbutyl 3-methylbutyl or the like, similar racemizations will be achieved.

What is claimed is:

1. A process for racemizing the pharmacologically less active enantiomer of a 5,6-dihydro-4-alkylamino-4H-thieno (or furo) [2,3-b] thiopyran-2-sulfonamide-7,7-dioxide which comprises HEATING an N-acyl derivative thereof in the presence of a base, selected from the group consisting of: (a) formamide used as a solvent; (b) an anhydrous base selected from tri($C_{1-3}$alkyl)-amine and an alkali metal $C_{1-3}$alkoxide in a protic solvent; followed by deacylation.

2. The process of claim 1 wherein the base is formamide used as solvent.

3. The process of claim 1 wherein the base is an anhydrous base selected from a tri($C_{1-3}$alkyl)amine and an alkali metal $C_{1-3}$alkoxide in a protic solvent.

4. The process of claim 1, wherein the pharmacologically less active enantiomer is a 5,6-dihydro-4-alkylamino-4H-thieno[2,3-b]thiopyran-2-sulfonamide-7,7-dioxide.

5. The process of claim 2 wherein the pharmacologically less active enantiomer is a 5,6-dihydro-4-alkylamino-4H-thieno[2,3-b]thiopyran-2-sulfonamide-7,7-dioxide.

6. The process of claim 3 wherein the pharmacologically less active enantiomer is a 5,6-dihydro-4-alkylamino-4H-thieno[2,3-b]thiopyran-2-sulfonamide-7,7-dioxide.

7. The process of claim 4, wherein the pharmacologically less active enantiomer is R(−)-5,6-dihydro-4-(2-methylpropyl)amino-4H-thieno[2,3-b]thiopyran-2-sulfonamide-7,7-dioxide.

8. The process of claim 5 wherein the pharmacologically less active enantiomer is R(−)-5,6-dihydro-4-(2- methylpropyl)amino-4H-thieno[2,3-b]thiopyran-2-sulfonamide-7,7-dioxide.

9. The process of claim 6 wherein the pharmacologically less active enantiomer is R(−)-5,6-dihydro-4-(2-methylpropyl)amino-4H-thieno[2,3-b]thiopyran-2-sulfonamide-7,7-dioxide.

10. The process of claim 1, wherein the acyl derivative is a trifluoroacetate.

11. The process of claim 2, wherein the acyl derivative is a trifluoroacetate.

12. The process of claim 3, wherein the acyl derivative is a trifluoroacetate.

13. The process of claim 4 wherein the acyl derivative is a trifluoroacetate.

14. The process of claim 5 wherein the acyl derivative is a trifluoroacetate.

15. The process of claim 6 wherein the acyl derivative is a trifluoroacetate.

16. The process of claim 7 wherein the acyl derivative is a trifluoroacetate.

17. The process of claim 8 wherein the acyl derivative is a trifluoroacetate.

18. The process of claim 9 wherein the acyl derivative is a trifluoroacetate.

* * * * *